(12) United States Patent
Marashdeh et al.

(10) Patent No.: US 10,281,422 B2
(45) Date of Patent: May 7, 2019

(54) DISPLACEMENT CURRENT PHASE TOMOGRAPHY FOR IMAGING OF LOSSY MEDIUM

(71) Applicants: Tech4Imaging LLC, Columbus, OH (US); Ohio State Innovation Foundation, Columbus, OH (US)

(72) Inventors: Qussai Mohammad Marashdeh, Columbus, OH (US); Geoffrey A. Legg, Tewksbury, MA (US); Christopher Edward Zuccarelli, Columbus, OH (US); Fernando Teixeira, Columbus, OH (US); Cagdas Gunes, Columbus, OH (US); Burak Gurlek, Istanbul (TR); Shah Chowdhury, Columbus, OH (US); Benjamin Straiton, Pataskala, OH (US); Joshua Sines, Hilliard, OH (US)

(73) Assignees: TECH4IMAGING LLC, Columbus, OH (US); OHIO STATE INNOVATION FOUNDATION, Columbus, OH (US)

( * ) Notice: Subject to any disclaimer, the term of this patent is extended or adjusted under 35 U.S.C. 154(b) by 275 days.

(21) Appl. No.: 15/262,565

(22) Filed: Sep. 12, 2016

(65) Prior Publication Data

US 2018/0074001 A1 Mar. 15, 2018

(51) Int. Cl.
*G01N 27/22* (2006.01)
*G01B 7/00* (2006.01)

(52) U.S. Cl.
CPC .................................. *G01N 27/22* (2013.01)

(58) Field of Classification Search
None
See application file for complete search history.

(56) References Cited

U.S. PATENT DOCUMENTS

| | | | |
|---|---|---|---|
| 5,130,661 A | 7/1992 | Beck et al. | |
| 5,262,730 A | 11/1993 | Smith et al. | |
| 5,279,163 A | 1/1994 | D'Antonio et al. | |
| 6,208,204 B1 | 3/2001 | Suzuki et al. | |

(Continued)

FOREIGN PATENT DOCUMENTS

| | | |
|---|---|---|
| CN | 102954854 A | 3/2013 |
| EP | 0606115 A1 | 7/1994 |

(Continued)

OTHER PUBLICATIONS

Marashdeh, et al., "On the ECT Sensor Based Dual Imaging Modality System for Electrical Permittivity and Conductivity Measurements", 2006, pp. 1-6, The Ohio State University, Columbus, Ohio.

(Continued)

*Primary Examiner* — Jermele M Hollington
(74) *Attorney, Agent, or Firm* — Standley Law Group LLP

(57) ABSTRACT

A system and method for Displacement Current Phase Tomography. The present system invention obtains a linear relationship between mutual displacement current from a sensor (output current of the measuring electrode terminals) and the area (or volume) of an object to be imaged in the imaging domain. The system uses capacitance sensors and utilizes the phase of the measured current, in addition to the amplitude, to reconstruct an image.

26 Claims, 9 Drawing Sheets

(56) References Cited

U.S. PATENT DOCUMENTS

| | | |
|---|---|---|
| 7,295,019 B2 | 11/2007 | Yang et al. |
| 7,424,462 B2 | 9/2008 | Avni et al. |
| 7,684,846 B2 | 3/2010 | Johnson et al. |
| 8,461,852 B2 | 6/2013 | Yang et al. |
| 8,508,238 B2 * | 8/2013 | Mahalingam ........ A61B 5/0536 324/603 |
| 8,519,722 B1 | 8/2013 | Prendergast |
| 8,614,707 B2 * | 12/2013 | Warsito ................ A61B 5/0535 345/419 |
| 8,762,084 B2 * | 6/2014 | Gao ..................... G01N 27/228 702/65 |
| 8,867,928 B2 | 10/2014 | Piehler |
| 9,016,143 B2 | 4/2015 | Mamigonians |
| 9,170,224 B2 | 10/2015 | Fan et al. |
| 9,259,168 B2 | 2/2016 | Marashdeh et al. |
| 9,579,038 B2 | 2/2017 | Brunner et al. |
| 9,581,560 B2 | 2/2017 | Fan et al. |
| 9,927,385 B2 * | 3/2018 | Marashdeh .......... G01N 27/228 |
| 2002/0028010 A1 | 3/2002 | Toida |
| 2003/0020493 A1 | 1/2003 | Haase et al. |
| 2003/0173958 A1 | 9/2003 | Goldfine et al. |
| 2004/0233191 A1 | 11/2004 | Mukherjee et al. |
| 2005/0167588 A1 | 8/2005 | Donnangelo |
| 2007/0024278 A1 | 2/2007 | Walters et al. |
| 2007/0133746 A1 | 6/2007 | Ortiz Aleman et al. |
| 2008/0116995 A1 | 5/2008 | Kim et al. |
| 2009/0272028 A1 | 11/2009 | Drozd et al. |
| 2010/0132473 A1 | 6/2010 | Willcox |
| 2010/0148804 A1 | 6/2010 | Jakoby et al. |
| 2010/0332170 A1 | 12/2010 | Gao et al. |
| 2011/0109911 A1 | 5/2011 | Podoleanu |
| 2012/0268135 A1 | 10/2012 | Marsala et al. |
| 2013/0187641 A1 | 7/2013 | Singer |
| 2013/0275082 A1 | 10/2013 | Follmer et al. |
| 2014/0361793 A1 | 12/2014 | Marashdeh et al. |
| 2014/0365152 A1 | 12/2014 | Marashdeh et al. |
| 2015/0338364 A1 | 11/2015 | Fan et al. |
| 2016/0025663 A1 | 1/2016 | Lehikoinen et al. |
| 2016/0091448 A1 | 3/2016 | Soleimani |
| 2016/0206227 A1 | 7/2016 | Marashdeh et al. |
| 2016/0310040 A1 | 10/2016 | Marashdeh |
| 2017/0241817 A1 * | 8/2017 | Marashdeh ................ G01F 1/64 |

FOREIGN PATENT DOCUMENTS

| | | |
|---|---|---|
| WO | 2010007096 A1 | 1/2010 |
| WO | 2011002793 A1 | 1/2011 |
| WO | 2015142610 A1 | 9/2015 |
| WO | 2015174975 A1 | 11/2015 |

OTHER PUBLICATIONS

Warsito, et al., "Electrical Capacitance Volume Tomography", 2007, pp. 1-9.

Covilakam, M., "Evaluation of Structural Monitoring Methods for Large Diameter Water Transmission Pipelines", Dec. 2011, The University of Texas at Arlington.

Chew, W. et al., Reconstruction of Two-Dimensional Permittivity Distribution Using the Distorted Born Iterative Method, IEEE Transactions on Medical Imaging, Jun. 1990, pp. 218-225, vol. 9, No. 2.

Marashdeh, Q. et al., Adaptive Electrical Capacitance Volume Tomography, IEEE Sensors Journal, Apr. 2014, pp. 1253-1259, vol. 14, No. 4.

Xie, C. et al., Electrical Capacitance Tomography for Flow Imaging: System Model for Development of Image Reconstruction Algorithms and Design of Primary Sensors, IEEE Proceedings-G, Feb. 1992, pp. 89-98, vol. 139, No. 1.

Yang, W. et al., Image Reconstruction Algorithms for Electrical Capacitance Tomography, Measurement Science and Technology 14, 2003, pp. R1-R13.

Huang et al., Design of Sensor Electronics for Electrical Capacitance Tomography, IEE Proceedings G (Circuits, Devices and Systems), vol. 139, Issue 1, Feb. 1992, p. 83-88.

Gunes, C. et al., A Comparison Between Electrical Capacitance Tomography and Displacement-Current Phase Tomography, IEEE Sensors Journal, Dec. 15, 2017, vol. 17, No. 24.

Wang,F. et al., Electrical Capacitance Volume Tomography: Design and Applications, Sensors, 2010 pp. 1890-1917.

Wikipedia, Electrical Capacitance Volume Tomography, https://en.wikipedia.org/w/index.php?title=Electrical_capacitance_volume_tomography&oldid=868112998, site visited Dec. 7, 2018.

* cited by examiner

Figure 1: System components

Figure 2: Receiver

Figure 4: Sensitivity matrix

Figure 5: Image reconstruction / Data reporting

Figure 6: Phase measured with moving sensor on a stationary object

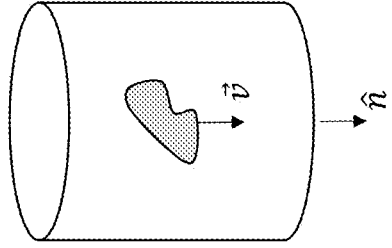
Figure 8: Velocity 3D mapping

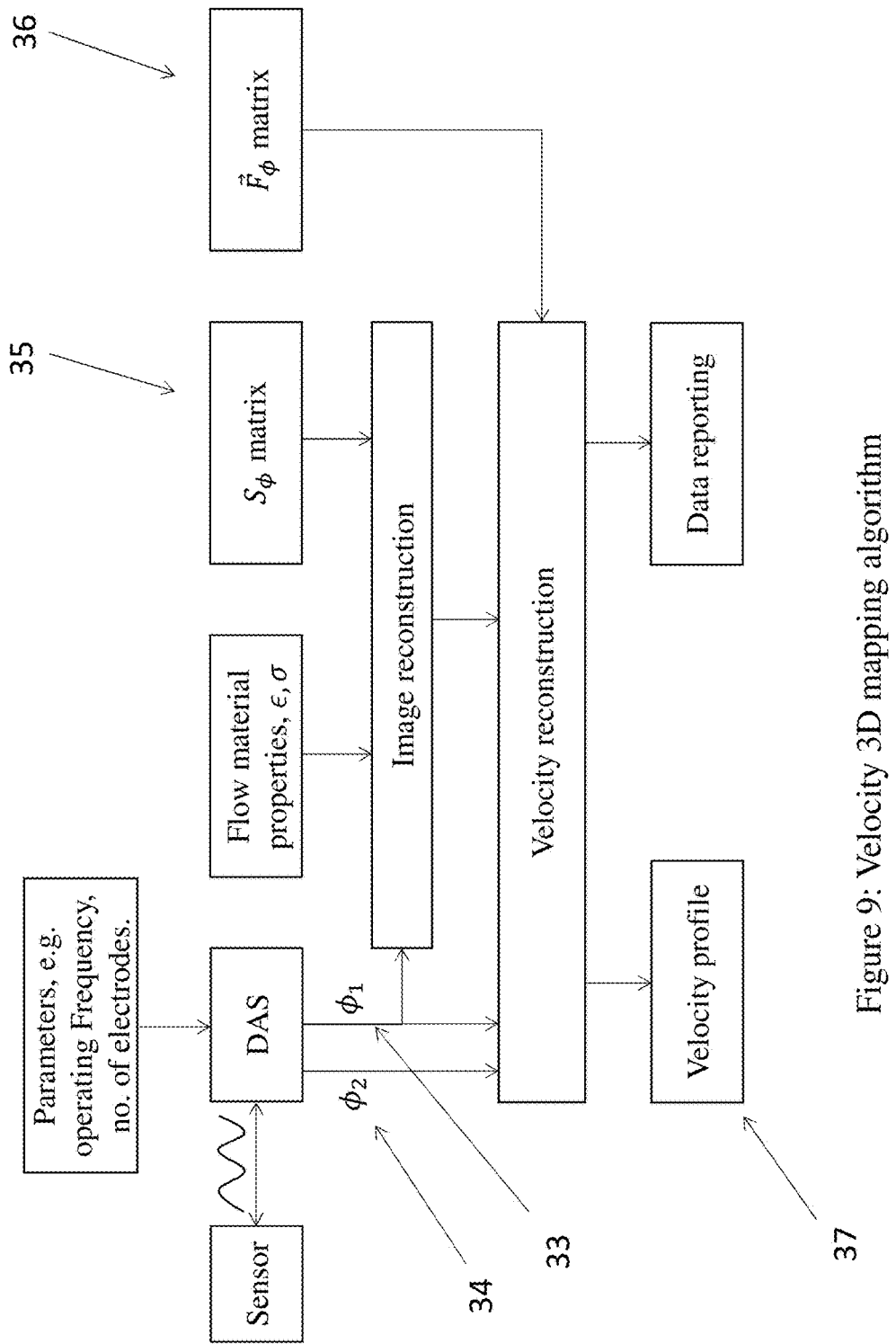
Figure 9: Velocity 3D mapping algorithm

DISPLACEMENT CURRENT PHASE TOMOGRAPHY FOR IMAGING OF LOSSY MEDIUM

STATEMENT REGARDING FEDERALLY SPONSORED RESEARCH OR DEVELOPMENT

This invention was made with government support under Contract NNX15CJ32P awarded by NASA. The Government has certain rights in the invention.

BACKGROUND AND SUMMARY OF THE INVENTIVE FIELD

Electrical Capacitance Volume Tomography (ECVT) is a non-invasive imaging modality. Its applications span an array of industries. Most notably, ECVT is applicable to multiphase flow applications commonly employed in many industrial processes. ECVT is often the technology of choice due to its advantages of high imaging speed, scalability to different process vessels, flexibility, and safety. In ECVT, sensor plates are distributed around the circumference of the column, object or vessel under interrogation. The number of sensor plates may be increased to acquire more capacitance data. However, increasing the number of sensor plates reduces the area of each sensor plate accordingly. A limit exists on the minimum area of a sensor plate for a given column diameter, thus limiting the maximum number of plates that can be used in an ECVT sensor. This limit is dictated by the minimum signal-to-noise ratio requirement of the data acquisition system. Since ECVT technology is based on recording changes in capacitance measurements induced by changes in dielectric distribution (i.e., phase distribution), and the capacitance level of a particular sensor plate combination is directly proportional to the area of the plates, minimum signal levels are needed to provide sufficiently accurate measurements. These considerations dictate the required minimum sensor plate dimensions. This limitation on the minimum size of the sensor plates, while increasing the number of available sensor plates in an ECVT sensor, is one of the main hurdles in achieving a high resolution imaging system.

To overcome this challenge, the concept of Adaptive Electrical Capacitance Volume Tomography (AECVT) was recently developed, whereby the number of independent capacitance measurements is increased through the use of reconfigurable synthetic sensor plates composed of many smaller sensor plates (constitutive segments). These synthetic sensor plates maintain the minimum area for a given signal-to-noise ratio (SNR) and acquisition speed requirements while allowing for many different combinations of (synthetic) sensor plates in forming a sensor plate pair.

Electrical Capacitance Tomography (ECT) is the reconstruction of material concentrations of dielectric physical properties in the imaging domain by inversion of capacitance data from a capacitance sensor. Electrical Capacitance Volume Tomography or ECVT is the direct 3D reconstruction of volume concentrations or physical properties in the imaging domain utilizing 3D features in the ECVT sensor design. An ECVT system is generally made up of a sensor, sensor electronics and a computer system for reconstruction of the image sensed by the sensor. An ECVT sensor is generally comprised of n electrodes or plates placed around a region of interest, in one embodiment providing n(n−1)/2 independent mutual capacitance measurements which are used for image reconstruction. Image reconstruction is performed by collecting capacitance data from the electrodes placed around the wall outside the vessel. ECVT technology is described in U.S. Pat. No. 8,614,707 to Warsito et al. which is hereby incorporated by reference.

Adaptive Electrical Capacitance Volume Tomography (AECVT) provides higher resolution volume imaging of capacitance sensors based on different levels of activation levels on sensor plate segments. In AECVT systems, electrodes are comprised of an array of smaller capacitance segments that may be individually addressed. For example, each segment may be activated with different amplitudes, phase shifts, or frequency to provide the desired sensitivity matrix distribution. The sensor electronics of the present invention is designed to detect and measure the capacitance for the adaptive ECVT sensor of the present invention. For example, the difference in electrical energy stored in the adaptive ECVT sensor would be measured between an empty state and a state where an object is introduced into the imaging domain (e.g., between the electrodes). In a preferred embodiment of the invention, the term "adaptive" means the ability to provide selective or high resolution control through the application of voltage or voltage distributions to a plate having an array of capacitance segments. The change in overall energy of the system due to the introduction of a dielectric material in the imaging domain is used to calculate the change in capacitance related to the dielectric material. The change in capacitance can be calculated from the change in stored energy. Sensor electronics can also be designed by placing individual segment circuits in parallel yielding a summation of currents representing total capacitance between segments under interrogation. By individually addressing the capacitance segments of the electrodes of the present invention, electric field distribution inside the imaging domain can be controlled to provide the desired sensitivity matrix, focus the electric field, and increase overall resolution of reconstructed images. Voltage distribution can also be achieved by using a conventional measuring circuit with a sensor that distributes voltages through a voltage divider.

In AECVT systems, a capacitance measurement circuit is connected to an electrode (detecting or receiving electrode) of the adaptive sensor so that a capacitance measurement can be obtained for the selected source and detecting electrodes. The capacitors Cx1–Cxn of the sensor represent the n number of capacitance segments of the selected source electrode and the detecting electrode. Each capacitance segment of the electrodes can be individually addressed by separated voltage sources. These voltage sources are used for regulating the voltage levels and phase shifts on the capacitance segments of each of the electrodes on the adaptive sensor. The voltage across each of the capacitor segments (Vxn) is the combination of the voltage source Vi and the voltage sources connected to each capacitor segment (Vn). Accordingly, the measured Vo can be used to calculate each of the equivalent capacitance (Cxn) of the capacitance segments of the activated electrode. The associated formula is for Cxn=Cx1=Cx2 . . . =Cxi. For segments with different capacitance values, the equivalent capacitance is calculated using the formula:

$$V_0 = \left(\frac{j\omega R_f}{1 + j\omega C_f R_f}\right)\left(\sum_{i=1}^{n} V_{xi} C_{xi}\right)$$

As discussed, in one embodiment, n(n−1)/2 independent mutual capacitance measurements are measured and used for image reconstruction. For example, the capacitance between each of the electrodes of the sensor are measured in turn and image reconstruction is performed using this capacitance data. In other words, capacitance measurements are obtained from every pair or electrode combination of the sensor, in turn, to be used in image reconstruction. It is appreciated that the voltage sources herein discussed may be connected to the capacitance segments of each of the electrodes of the sensor array using known switch technologies. Using switches, the system can selectively choose which electrodes to activate by connecting the voltage sources to the selected electrodes through the switches. In another embodiment, switching or multiplexing circuit elements can be used to connect the appropriate voltage sources to each of the capacitance segments of the selected electrode allowing various elements to be selectively connected to each capacitance segment depending on the focus and sensitivity desired. For example, voltage sources of greater amplitude may be switched or connected to the capacitance segments in the center of the electrode or imaging domain so as to focus the measurements towards the center of the electrode or imaging domain.

In an alternate embodiment, instead of using different amplitudes, different frequencies may be used to activate electrode segments enabling concurrent measurements of different capacitance values introduced by electric field beams of different frequencies. In yet another alternate embodiment, different phase shifts may be used to activate electrode segments enabling steering of the electric field inside the imaging domain. The measured change in output voltage can be used to calculate the change in capacitance levels between the capacitance segments which are then used to reconstruct volume images of objects or materials between the sensors. AECVT is described in U.S. Pat. No. 9,259,168 to Marashdeh et al. which is hereby incorporated by reference.

In ECT, ECVT, or AECVT, the capacitance measurement between sensor plates is also related to the effective dielectric content between that plate pair. The SART method can be extended to all measurements of ECT, ECVT, or AECVT sensors, thus providing a high resolution visual representation of each phase through image reconstruction. These previous ECVT systems incorporate data acquisition system that increase imaging resolution through sensing capacitances from 3D conventional and adaptive capacitance sensors. Data acquisition systems are also described in U.S. patent application Ser. No. 14/191,574 (Publication No. US-2014-0365152-A1) which is hereby incorporated by reference.

Electrical capacitance sensors are used for non-invasive imaging by distributing the electric field inside the imaging domain in 3D. ECVT sensors enable sensitivity variation in the imaging domain that can utilize different plate shapes and distributions to target a volume for imaging.

Tomography systems are categorized as hard field or soft field modalities. In the former, the measured signal is directly attributed to material distribution in the imaging domain. Whereas in the latter, the measured signal is indirectly related to the material distribution. This indirect relation in soft field tomography complicates the image reconstruction problem resulting in lower imaging resolution when compared to hard field tomography. Electrical Capacitance Volume Tomography (ECVT) is a soft field modality in which the measured signal is related to the material permittivity distribution through the electric field distribution. The electric field distribution changes as a function of material permittivity distribution yielding a non-direct relation between material distributions and measured signal from the ECVT sensors. This effect extends to all cases where electric capacitance sensors are used, including in Adaptive ECVT (AECVT).

There have been some efforts to design new reconstruction algorithms for ECVT based on sensor co-design in which the sensor activation is updated electronically based on reconstructed image and flow conditions. Nevertheless, the non-linearity of the problems is still present and such algorithms have difficulty in applications including higher permittivity materials (e.g. water). Materials with high permittivity (dielectric constant) amplify the non-linearity in the image reconstruction problem further complicating extracting an image from the measured signal. There is a need for a sensor design or reconstruction algorithm that is able to provide quantitatively accurate results for the permittivity distribution once there is a high dielectric contrast in the system. This constitutes an important challenge in ECVT since many flow processes may involve water, for example, which, as noted, has a very large dielectric constant. The image reconstruction process here is required to gauge both the material distribution and the electric field distribution that is shaped by the material distribution. This convoluted relation makes extracting a high resolution image from capacitance tomography sensors extremely difficult.

The present invention relates to a system and process to obtain a linear relationship between mutual displacement current from the sensor (output current of the measuring electrode terminals) and the area (or volume) of an object to be imaged in the imaging domain. This new system uses capacitance sensors and utilizes the phase of the measured current, in addition to the amplitude, to reconstruct an image. This new system is named Displacement Current Phase Tomography (DCPT). Similar to ECVT, DCPT is a low-cost imaging modality with the potential of being very useful to image two or three phase flow systems where there is a high contrast in the dielectric constant or where the material being imaged is lossy due to presence of electric conductivity or dielectric loss.

Linearity of the phase measurement in response to a lossy medium with high dielectric constant has been established by analytic derivation, computer simulations, and experiments. In the analytical derivation, a two capacitance plate problem is considered where the area between the two plates is partially filled with water. In conventional ECVT, the basic measurement parameter is the current amplitude across the capacitor plates, which can be used to determine the mutual capacitance between plates and consequently employed in a reconstruction algorithm. When objects to be imaged in the imaging domain are lossy (i.e., having electric conductivity or dielectric loss), there is additional information contained in the phase of the currents that can be exploited for reconstruction. The variation of the current phase is nearly linear with the object volume (volume fraction) for many lossy materials. For the reconstruction process in ECVT, it is important to establish the sensitivity map based on the phase information. The traditional sensitivity map connects the capacitance (current amplitude) measurements to the permittivity distribution in the imaging domain via a linear approximation. The phase information, with its linear relation to material distribution, provides an alternative imaging resolution using such linearized sensitivity matrix. The conventional sensitivity map encodes the variation on the capacitance measurement due to a small variation (pixel) on the permittivity distribution. In order to use the phase information for DCPT imaging, the role of capacitance and conductivity (or dielectric loss) on stored electromagnetic energy is examined. In general, the quasi-static admittance Y can be expressed in the terms of the average dissipated power and the average stored energy in the electric field as $$Y = \frac{2}{|V|^2}(<P_d> + j2\omega <W_e>) = Y_R + jY_I \quad (1)$$

with the averaged dissipated power expressed as $$<P_d> \geq \frac{1}{2}\iiint \sigma |\nabla \phi|^2 dV \quad (2)$$

and the average stored energy in the electric field expressed as $$<W_e> \geq \frac{1}{4}\iiint \epsilon |\nabla \phi|^2 dV \quad (3)$$

where the integrals above are taken for the electric potential φ in the imaging domain and the averages are taken over one cycle. Assuming a unit voltage excitation, V=1, for the sender electrode plate, with all other plates grounded, the phase of the current measured at a receiver plate will then be simply equal to the phase of the admittance Y, that is:

$$\varphi = \tan^{-1}\left(\frac{<P_d>}{2\omega <W_e>}\right) \quad (4)$$

The real and imaginary terms in the expression for the admittance in equation (1) are related to the amplitude and phase of measured displacement current. As noted from (1), (2) and (3), the real and the imaginary parts of the admittance are related to conductivity and permittivity respectively.

In the DCPT system, the phase of the measured current signal serves as the basic parameter used to perform the image reconstruction. Image reconstruction algorithms in ECVT and DCPT employ the sensitivity matrix to map variations of the measured parameter (permittivity in ECVT and conductivity or dielectric loss in DCPT) with respect to variations of the distribution to be reconstructed on a pixel (voxel) in the region of interest. The phase sensitivity matrix for materials with low dielectric loss is defined as:

$$S_{x,y,z} = \frac{\Delta \varphi}{\Delta p_{x,y,z}}$$

where $$p_{x,y,z} = \frac{\sigma_{x,y,z}}{\omega \epsilon_{x,y,z}},$$

and the x, y, and z are the location of the voxel at which the phase sensitivity is being calculated.

Similar to conventional capacitance tomography, the phase sensitivity matrix thus formed at all pixel locations is used together with the measurement of the current phase to reconstruct the material distribution (spatial distribution of the conductivity or dielectric loss) in the region of interest.

The phase information can also be used to infer velocity of a moving material in the imaging domain. Depending on the material conductive and dielectric properties, a relaxation time exists between when the electric field is applied to the material and when the material fully responds in dielectric polarization. As the moving material enters the volume between the sensor plates and then exits, the material will still be polarized after it exits and will relax based on its relaxation time constant. This residual relaxation happening outside the sensor plate's effective zone will produce a change in the phase of the measured current. Consequently, changes in the measured displacement current phase of the sensor when material is moving inside the sensor can be directly related to velocity of moving material. This phenomenon can also be used to measure velocity of a continuous single material flowing in the imaging domain (i.e., a moving water column or moving solids) where the effective dielectric constant does not change. Measuring the velocity of a single material flow has been a challenge in capacitance tomography as the change in effective dielectric constant is used to track flow velocity. Since effective dielectric constant does not change in a single material flow, capacitance tomography is not able to measure a significant change in signal related to velocity. DCPT solves this problem by using changes in the measured current phase as an indicator of flow velocity when the effective dielectric constant inside the imaging domain does not change.

The measured current phase is also a function of excitation frequency applied to the sender electrodes of the sensor. Changes in phase as a function of frequency can also be used to image multiple materials in the imaging domain similar to the Multi-Phase Flow Decomposition approach used previously. For example, as described in patent application Ser. No. 15/138,751, changes in effective dielectric constants at various frequencies have been used to image more than two materials in the imaging domain. In this invention, changes in phase measurement at different frequencies can likewise be used to image more than two materials in the imaging domain.

In previous ECVT systems, conductivity in the imaging domain is imaged by measuring the real-part of the current signal or the power loss. In this invention, the phase of the measured current and not the real part of the measured current is used as the measured signal for image reconstruction and velocity mapping.

In one embodiment of the invention, the invention is comprised of a three-dimensional capacitance sensor device comprising a plurality of electrodes for placement around a vessel or object, wherein the three-dimensional capacitance sensor device is adapted to provide electric field distribution and sensor sensitivity in three geometric dimensions; data acquisition electronics in communication with the three-dimensional capacitance sensor device for receiving current output from the three-dimensional capacitance sensor device and for outputting phase data for the current; a processing system in communication with the data acquisition electronics, the processing system programmed with instructions for executing on the processing system to reconstruct a three-dimensional volume-image from the phase data generated by the data acquisition electronics.

In one embodiment, the data acquisition electronics is further comprised of a current to voltage converter for receiving the current output from the three-dimensional capacitance sensor device; a gain amplifier in electrical communication with the current to voltage converter; an analog to digital converter in electrical communication with the gain amplifier; and a synchronous demodulation circuit in electrical communication with the analog to digital converter.

The phase measurement between different electrode pairs of different geometries can also be used to map 3D velocities of a moving continuous single material flowing in the imaging domain. For example, 3D velocities and vortex loops in a continuous flow of water can be imaged using measured phase from different plate pairs in ECVT or AECVT sensors using the DCPT approach.

In one embodiment, the phase measurement from each plate pair of the sensor is first converted into volume fraction. The new volume fraction signal from all sensor plate combinations is then used for image reconstruction and estimation of total material in the imaging domain. The volume fraction of each plate pair refers to the percentage of volume covered by said plate pair.

In some cases, Electrical Impedance Tomography (EIT) can also be used to image domains with conductive materials, however, in contrast to EIT, DCPT measures the displacement current across electrodes as opposed to conduction current in EIT. As such, DCPT does not require any electrical contact whatsoever between the hardware sensor and the domain to be imaged, as opposed to EIT, which is predicated on the existence of an electrical contact. In addition, DCPT is easily applicable for the imaging of multiphase flows with air or vacuum comprising the continuum phase, whereas EIT is not feasible for such problems since a conduction current cannot be then established across the domain. These characteristics of DCPT immediately opens up the number of applications for which DCPT is useful but EIT is not. DCPT is also different than conventional Electrical Capacitance Tomography (ECT) as ECT uses the displacement current amplitude for image reconstruction and data analysis whereas DCPT uses the phase of the displacement current.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 8 illustrates a method for generating 3D velocity maps from measured phase data.

FIG. 9 illustrates a method for generating 3D velocity maps from measured phase data.

DETAILED DESCRIPTION OF EXEMPLARY EMBODIMENT(S)

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1:
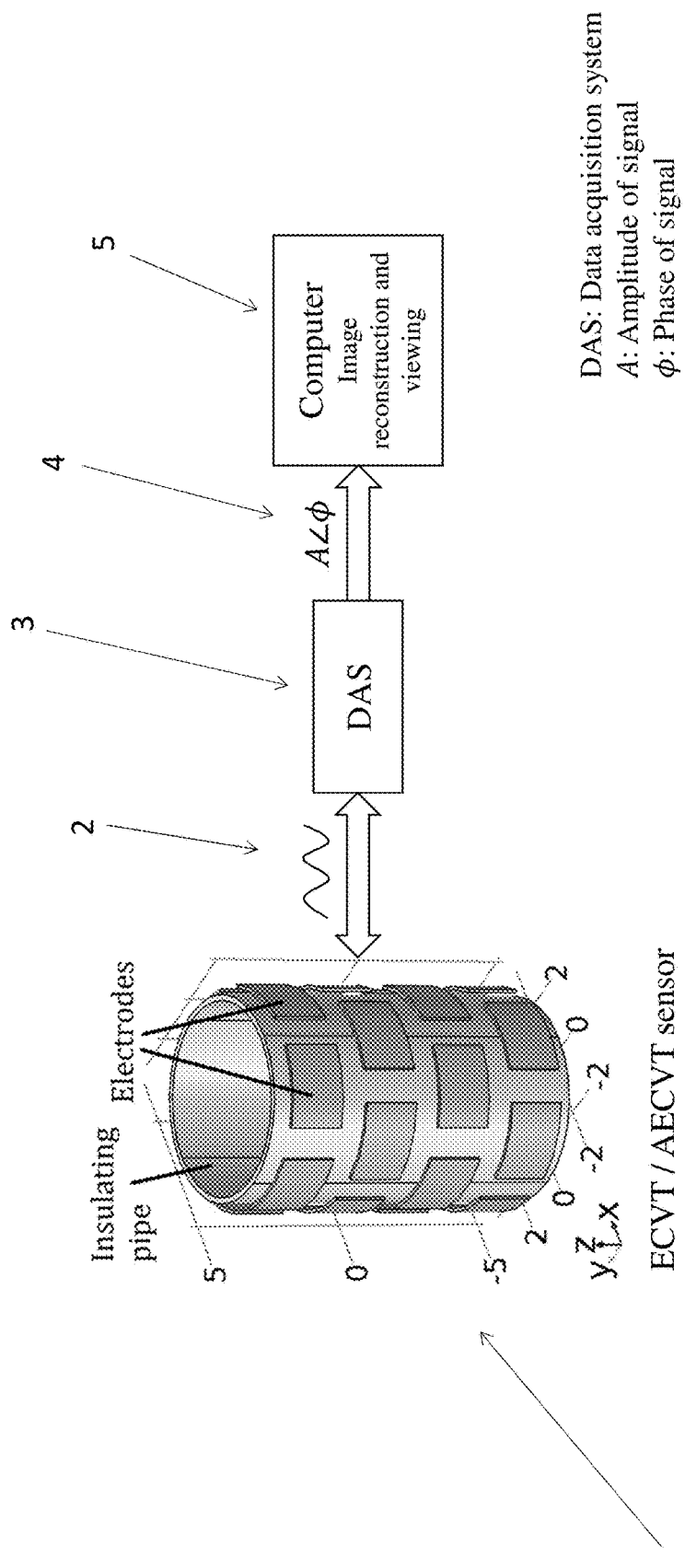
FIG. 1 illustrates one embodiment of a DCPT system including the sensor, Data Acquisition System (DAS), and computer for data processing and image reconstruction.

FIG. 1 illustrates one embodiment of DCPT system composed of sensor (1), DAS (3), and computing device for image reconstruction and data analysis (5). The DAS receives a sinusoidal signal from sensor (2) and reports its amplitude and phase (4) to computing device. In this invention, the phase signal is used for image reconstruction, velocity mapping, and data analysis. Material inside the sensor imaging domain is with conductivity or dielectric loss. The reported phase from different sensor plate combination depends both on the material property and its location in the imaging domain.

Figure 2:
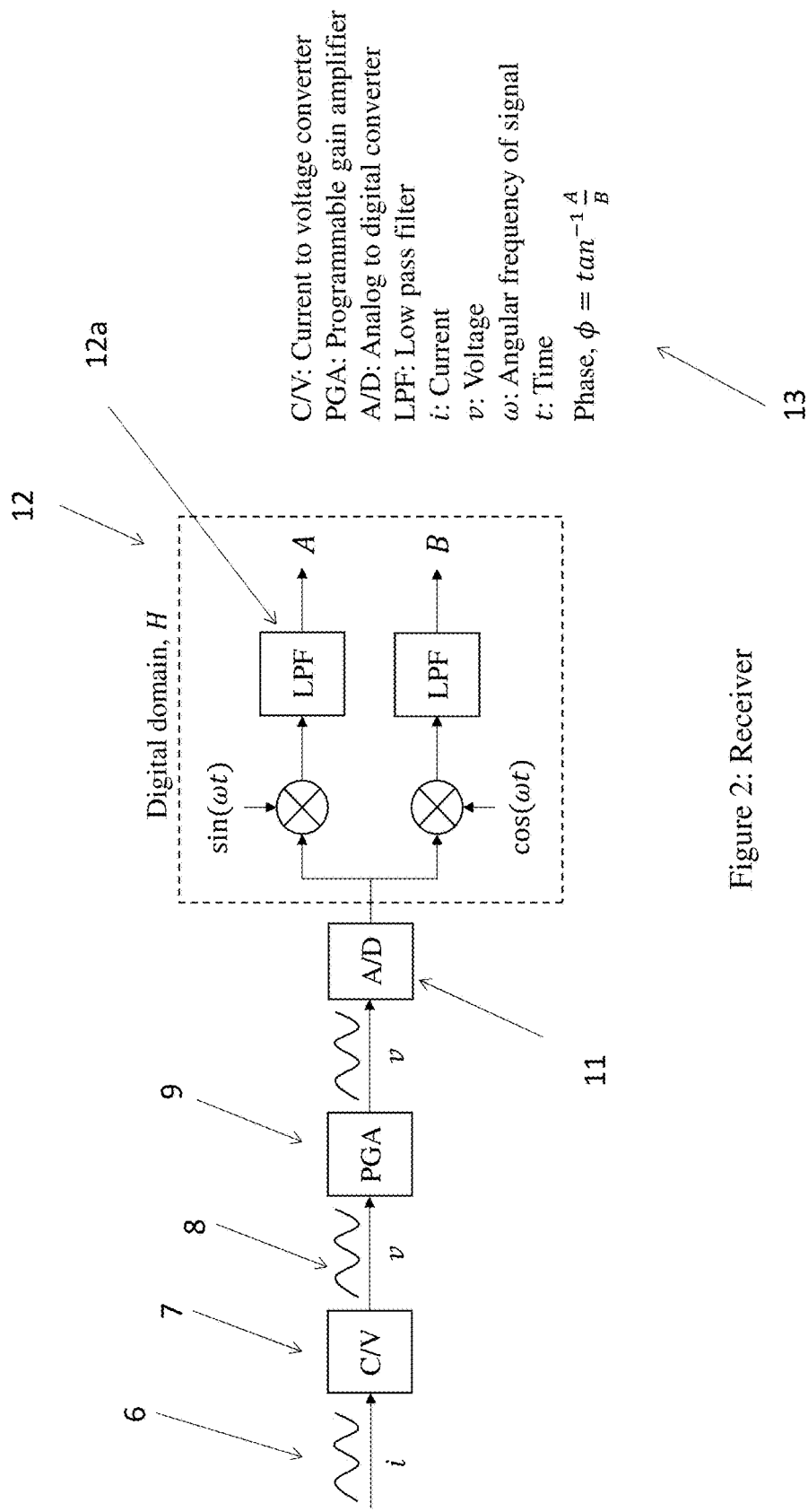
FIG. 2 illustrates one embodiment of the DAS receiver path where measured displacement current is used to calculate phase shift.

FIG. 2 illustrates one embodiment of the DAS receiver path where measured displacement current is used to calculate phase shift. FIG. 2 illustrates one embodiment of a receiver chain in the DAS that converts sinusoidal displacement current (6) to amplitude and phase in digital format. The current is first converted to a sinusoidal voltage (8) using current to voltage amplifier (7). The voltage is then amplified using a programmable gain amplifier (9) and converted to digital format using an analog to digital converter (11). The phase is calculated from a synchronous demodulation block implemented in the digital domain (12). The synchronous demodulation block has low pass filters (12a) to filter out high frequency components of the signal.

Figure 3:
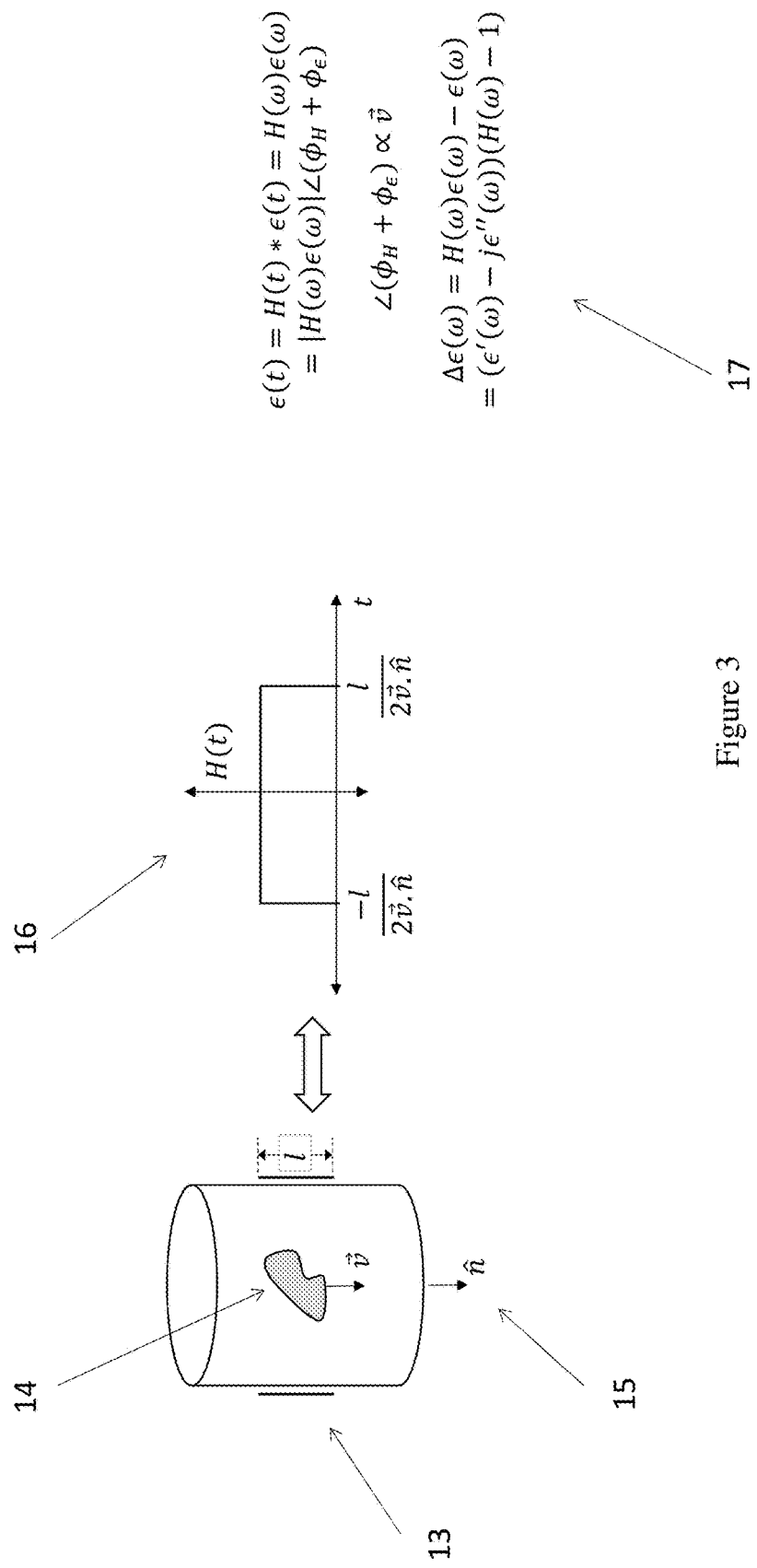
FIG. 3 illustrates one embodiment of a method of using measured phase to estimate velocity of moving material or object.

FIG. 3 illustrates the change in displacement current phase as a function of velocity and sensor design. FIG. 3 illustrates one embodiment of a method of using measured phase in FIG. 2 to estimate velocity of moving material or object (14). Here, the phase is related to sensor geometric formation (13), the normal vector to the volume of electric field between the sensor plates (15) and velocity of moving object (14). Those parameters are used to construct a transfer function (16) that is convoluted with dielectric time response to relate measured phase with velocity (17).

Figure 4:
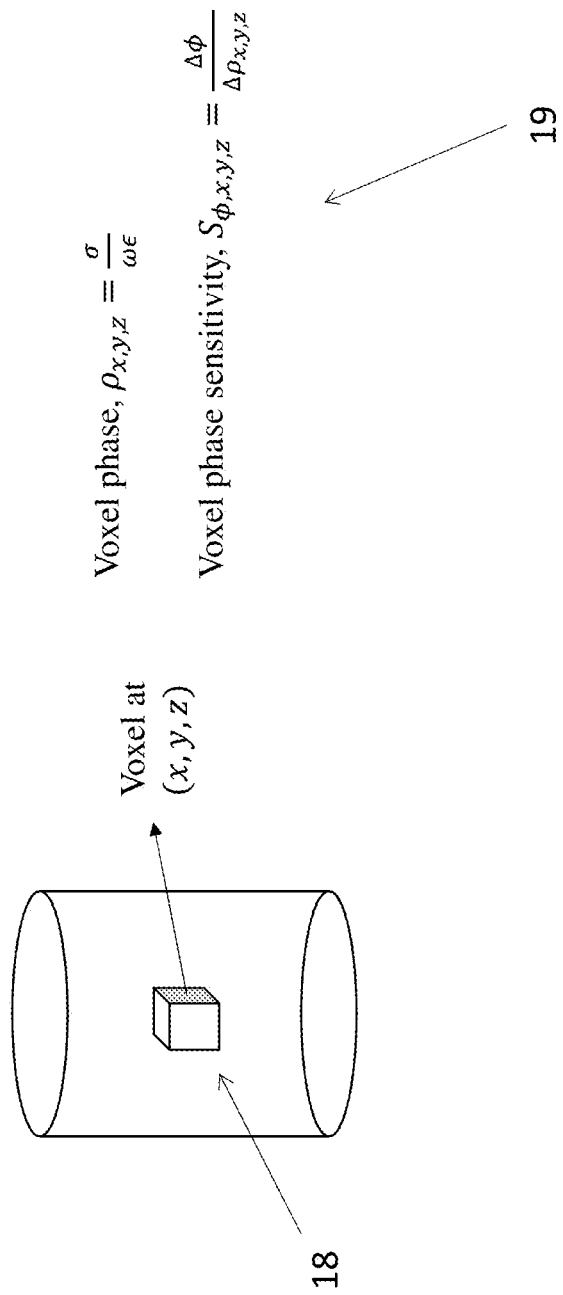
FIG. 4 illustrates one embodiment of the sensitivity matrix calculated at one voxel location in the imaging domain.

FIG. 4 illustrates one embodiment of calculating the sensitivity matrix at a one voxel location (18). The sensitivity matrix value at this location is the ratio between change in phase to change in electric properties of voxel at specified location (19).

Figure 5:
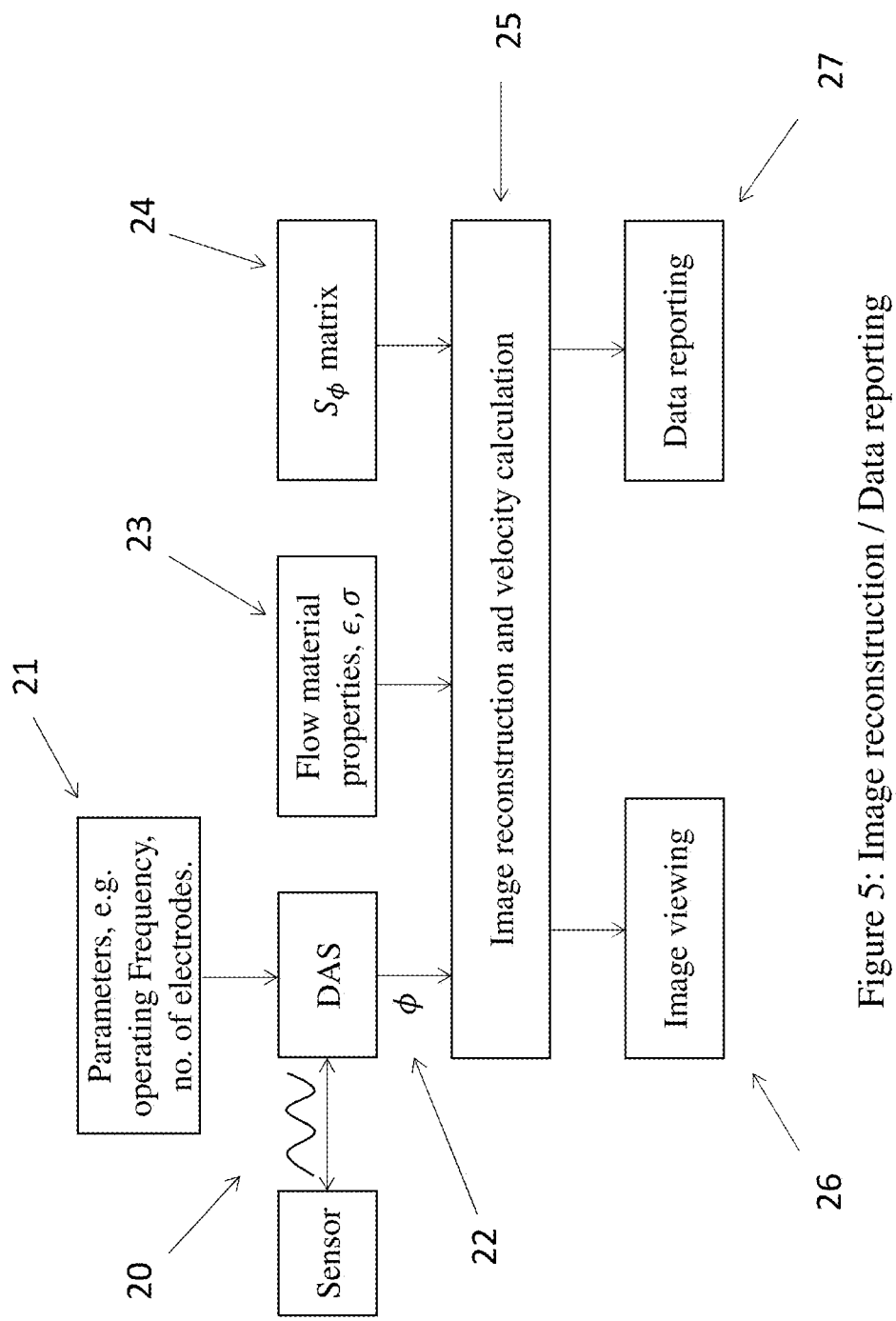
FIG. 5 illustrates a process for using phase of displacement current for image reconstruction and data reporting.

FIG. 5 illustrates a process for using phase of displacement current for image reconstruction and data reporting. The DAS uses parameters (21) selected by users to activate the sensors and receive a sinusoidal current (20). The DAS provides the phase of measured current in digital format (22) to the image reconstruction and velocity calculation block (25). The image reconstruction is performed using knowledge of flow parameters (23) and sensitivity matrix of the sensor (24). The result of image reconstruction is used for image viewing (26), image analysis, and data reporting of materials inside the imaging domain (27).

Figure 6:
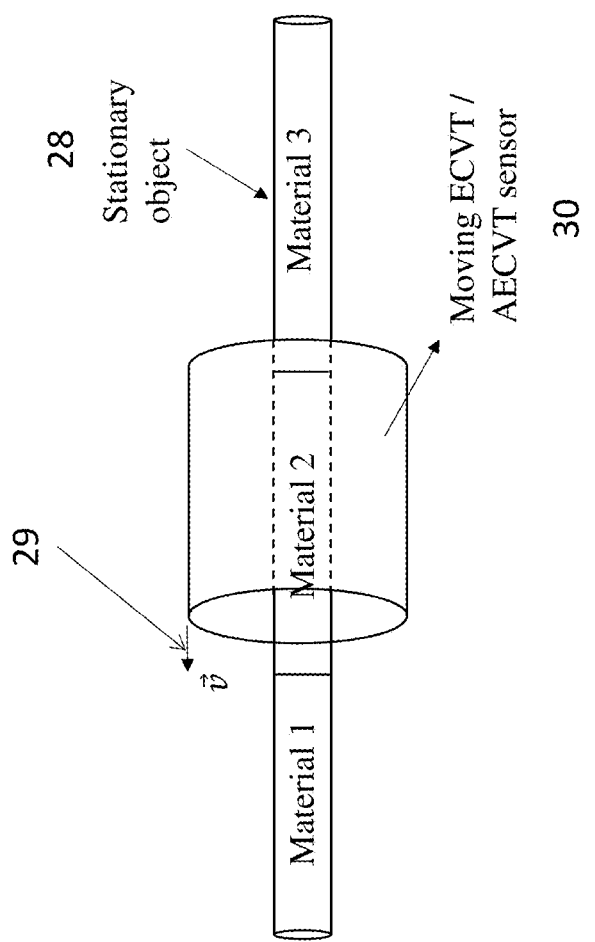
FIG. 6 illustrates one embodiment of measuring phase for inspecting a stationary object by moving the sensor over the object.

FIG. 6 illustrates one embodiment of measuring phase for inspecting a stationary object by moving the sensor over the object. FIG. 6 illustrates introducing a phase change in a measured current from the ECVT sensor (30) by moving it with a known velocity over a static pipe, conduit, or structure. Moving the sensor generates phase change similar to the object moving with the sensor being stationary. The change in phase in this case is directly related to velocity of the sensor (29) and materials inside the stationary object (28). Knowing the velocity of the sensor enables attributing phase changes in measured current to changes in materials inside stationary object.

Figure 7:
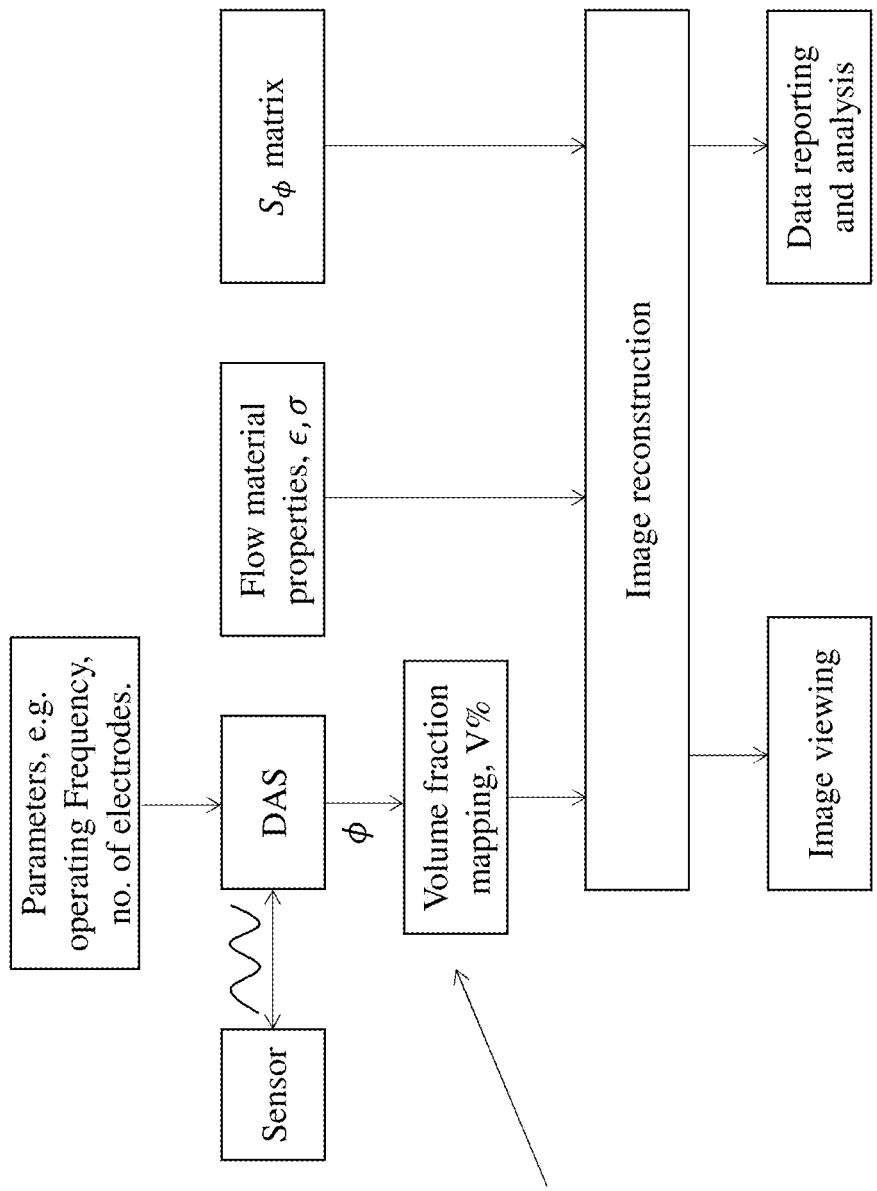
FIG. 7 illustrates one embodiment of a process of converting phase measurements from each sensor plate pairs to a volume fraction percentage and then using the volume fraction signal for image reconstruction and data analysis.

FIG. 7 illustrates a flow chart of data analysis and image reconstruction based on phase signal, similar to FIG. 5 with an added block to convert phase measurement from each plate combination in the sensor to volume fraction occupied by material (31). FIG. 7 illustrates one embodiment of a process of converting phase measurements from each sensor plate pairs to a volume fraction percentage and then using the volume fraction signal for image reconstruction and data analysis.

FIG. 8 illustrates a methodology for velocity 3D mapping based on phase measurement (32). Here, a gradient of the velocity sensitivity is considered for relating flow velocity to changes in phase measurements.

FIG. 9 illustrates a flow chart that details reconstructing 3D velocity maps from phase measurements. Phase measurement from the sensor at time t1 (33) is used for image reconstruction of flow distribution using a phase sensitivity matrix (35). The difference between phase measurement at time t1 (33) and phase measurement at time t2 (34) is used with the gradient sensitivity matrix (36) to reconstruct a 3D velocity vector map or velocity profile (37). Here, a gradient of the velocity sensitivity is considered for relating flow velocity to changes in phase measurements.

While certain embodiments of the present invention are described in detail above, the scope of the invention is not to be considered limited by such disclosure, and modifications are possible without departing from the spirit of the invention as evidenced by the following claims.

What is claimed is:

1. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions;
data acquisition electronics in communication with the three-dimensional capacitance sensor device for receiving current output from the three-dimensional capacitance sensor device and for outputting phase data for the current;
a processing system in communication with the data acquisition electronics, the processing system programmed with instructions for executing on the processing system to reconstruct a three-dimensional volume-image from the phase data generated by the data acquisition electronics; and
wherein the plurality of electrodes are configured to be placed around a pipe, tube or object, each electrode comprising a plurality of capacitance plate segments, and wherein the system is further comprised of:
a voltage source; and
wherein the plurality of electrodes is comprised of: a first electrode, having a plurality of capacitance plate segments that are addressable with the voltage source; a second electrode, having a plurality of capacitance plate segments, the capacitance plate segments of the second electrode electrically coupled to the measurement circuit; and wherein the capacitance plate segments of the first electrode form capacitance pairs with at least one of the capacitance plate segments of the second electrode when activated;
and wherein the system is adapted to collect capacitance data by:
defining a capacitor by using a capacitance plate segment on the first electrode as a source electrode, using a capacitance plate segment on the second electrode as a detecting electrode,
charging and discharging the defined capacitor by directing a predetermined voltage to the source electrode from the voltage source;
detecting a capacitance of the defined capacitor by detecting a current induced in the detecting electrode.

2. The system according to claim 1, wherein the three-dimensional capacitance sensor device is comprised of at least two planes of electrodes to provide sensor sensitivity in the axial and radial directions.

3. The system according to claim 1, wherein the processing system is programmed with an image reconstruction algorithm.

4. The system according to claim 1, wherein the image reconstruction algorithm is adapted to provide real-time imaging of multiphase flow within the vessel.

5. The system according to claim 1, wherein the processing system is programmed to calculate capacitance data from the input data received by the data acquisition electronics.

6. The system according to claim 1, wherein the processing system is programmed with instructions for executing on the processing system to reconstruct a three-dimensional volume-image of moving flows and stationary objects by analyzing the phase change of the current from the capacitance sensor device.

7. The system according to claim 1, wherein the processing system is programmed with instructions for executing on the processing system to measure velocity of flows that do not undergo changes in effective dielectric constant.

8. The system according to claim 1, wherein a sensitivity matrix is generated for the system by recording changes in phase with respect to changes in electric properties of flow materials.

9. The system according to claim 1, wherein the data acquisition electronics is further comprised of a synchronous demodulation circuit adapted to track phase changes in the current.

10. The system according to claim 8, wherein the processing system is programmed with instructions for executing on the processing system to use a gradient of phase sensitivity matrix to generate a three-dimensional (3D) velocity map based on phase measurements.

11. The system according to claim 1, wherein the three-dimensional capacitance sensor device is adapted to be operated at multiple frequencies simultaneously for probing material in the three-dimensional capacitance sensor device using differences in phases from various activation frequencies.

12. The system of claim 1, wherein the system is adapted to control the sensitivity of the three-dimensional capacitance sensor device by changing the frequency of the voltage distribution applied to at least one electrode.

13. The system of claim 1, wherein the data acquisition electronics is further comprised of:

a current to voltage converter for receiving the current output from the three-dimensional capacitance sensor device;
a gain amplifier in electrical communication with the current to voltage converter;
an analog to digital converter in electrical communication with the gain amplifier;
a synchronous demodulation circuit in electrical communication with the analog to digital converter.

14. The system of claim 1, wherein the synchronous demodulation circuit is further comprised of low pass filters to filter out high frequency components of a signal received at an input to the synchronous demodulation circuit.

15. The system of claim 1, wherein the three-dimensional capacitance sensor device is adapted to be moved over a stationary object at a predetermined velocity and wherein the system is adapted to determine phase changes in the current.

16. The system of claim 15, wherein the processing system is programmed with instructions for executing on the processing system to reconstruct a three-dimensional volume-image from the phase changes.

17. The system of claim 1, wherein the processing system is programmed with instructions for executing on the processing system to convert the phase data to volume fraction occupied by material in the three-dimensional capacitance sensor device.

18. The system of claim 1, wherein the processing system is programmed with instructions for executing on the processing system to generate a three-dimensional (3D) velocity map by using the difference between two different phase measurements at two different times with a gradient sensitivity matrix.

19. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions;
data acquisition electronics in communication with the three-dimensional capacitance sensor device for receiving current output from the three-dimensional capacitance sensor device and for outputting phase data for the current;
a processing system in communication with the data acquisition electronics, the processing system programmed with instructions for executing on the processing system to reconstruct a three-dimensional volume-image from the phase data generated by the data acquisition electronics; and
wherein the data acquisition electronics is further comprised of:
a current to voltage converter for receiving the current output from the three-dimensional capacitance sensor device;
a gain amplifier in electrical communication with the current to voltage converter;
an analog to digital converter in electrical communication with the gain amplifier;
a synchronous demodulation circuit in electrical communication with the analog to digital converter, the synchronous demodulation circuit adapted to track phase changes in the current.

20. The system of claim 19, wherein the three-dimensional capacitance sensor device is adapted to be moved over a stationary object at a predetermined velocity and wherein the system is adapted to determine phase changes in the current.

21. The system of claim 20, wherein the processing system is programmed with instructions for executing on the processing system to reconstruct a three-dimensional volume-image from the phase changes.

22. The system of claim 20, wherein the processing system is programmed with instructions for executing on the processing system to convert the phase data to volume fraction occupied by material in the three-dimensional capacitance sensor device.

23. The system of claim 20, wherein the processing system is programmed with instructions for executing on the processing system to generate a three-dimensional (3D) velocity map by using the difference between two different phase measurements at two different times with a gradient sensitivity matrix.

24. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions;
data acquisition electronics in communication with the three-dimensional capacitance sensor device for receiving current output from the three-dimensional capacitance sensor device and for outputting phase data for the current;
a processing system in communication with the data acquisition electronics, the processing system programmed with instructions for executing on the processing system to reconstruct a three-dimensional volume-image from the phase data generated by the data acquisition electronics;
wherein the data acquisition electronics is further comprised of:
a current to voltage converter for receiving the current output from the three-dimensional capacitance sensor device;
a gain amplifier in electrical communication with the current to voltage converter;
an analog to digital converter in electrical communication with the gain amplifier;
a synchronous demodulation circuit in electrical communication with the analog to digital converter.

25. The system of claim 24, wherein the processing system is programmed with instructions for executing on the processing system to convert the phase data to volume fraction occupied by material in the three-dimensional capacitance sensor device.

26. The system of claim 24, wherein the processing system is programmed with instructions for executing on the processing system to generate a three-dimensional (3D) velocity map by using the difference between two different phase measurements at two different times with a gradient sensitivity matrix.

* * * * *